United States Patent
Heitz et al.

(10) Patent No.: US 11,655,228 B2
(45) Date of Patent: *May 23, 2023

(54) PROCESS FOR PREPARING DIOXOLANE

(71) Applicants: BASF SE, Ludwigshafen am Rhein (DE); Kolon Plastics Inc., Gwacheon-Si (KR)

(72) Inventors: Thomas Heitz, Ludwigshafen am Rhein (DE); Marvin Kramp, Ludwigshafen am Rhein (DE); Manfred Heilig, Ludwigshafen am Rhein (DE); HyunSoo Chang, Gimcheon (KR); JongMoon Kim, Gimcheon (KR); In Gi Cho, Gimcheon (KR)

(73) Assignees: BASF SE, Ludwigshafen am Rhein (DE); Kolon Plastics Inc., Gwacheon-Si (KR)

( * ) Notice: Subject to any disclaimer, the term of this patent is extended or adjusted under 35 U.S.C. 154(b) by 132 days.

This patent is subject to a terminal disclaimer.

(21) Appl. No.: 17/056,741

(22) PCT Filed: May 8, 2019

(86) PCT No.: PCT/EP2019/061773
§ 371 (c)(1),
(2) Date: Nov. 18, 2020

(87) PCT Pub. No.: WO2019/219468
PCT Pub. Date: Nov. 21, 2019

(65) Prior Publication Data
US 2021/0403447 A1    Dec. 30, 2021

(30) Foreign Application Priority Data
May 18, 2018 (EP) .................... 18173076

(51) Int. Cl.
*C07D 317/12* (2006.01)
(52) U.S. Cl.
CPC .................. *C07D 317/12* (2013.01)
(58) Field of Classification Search
USPC ....................................................... 549/430
See application file for complete search history.

(56) References Cited

U.S. PATENT DOCUMENTS 5,695,615 A    12/1997 Thigpen
7,754,900 B2    7/2010 Siegert et al.

FOREIGN PATENT DOCUMENTS

| | | |
|---|---|---|
| CN | 1149055 A | 5/1997 |
| DE | 102005042505 A1 | 3/2007 |
| EP | 0867434 A1 | 9/1998 |
| WO | WO-2012177598 A1 | 12/2012 |
| WO | WO-2019219475 A1 | 5/2019 |

OTHER PUBLICATIONS

Dong et al., ACS Omega (2018) vol. 3, pp. 4974-4985.*
International Search Report for PCT/EP2019/061773 dated Jul. 1, 2019.
International Search Report for PCT/EP2019/061784 dated Jun. 21, 2019.
Written Opinion of the International Searching Authority for PCT/EP2019/061773 dated Jul. 1, 2019.
Written Opinion of the International Searching Authority for PCT/EP2019/061784 dated Jun. 21, 2019.

* cited by examiner

*Primary Examiner* — Taofiq A Solola
(74) *Attorney, Agent, or Firm* — Faegre Drinker Biddle & Reath LLP

(57) ABSTRACT

The present invention relates to a process for preparing dioxolane by reacting ethylene glycol with an aqueous solution of formaldehyde in the presence of an acid catalyst. The raw product comprising water, dioxolane and methanol is fed to a phase separation unit (20) wherein an organic extracting agent is present. An organic fraction stream from the phase separation unit is transferred to an upper part of a purification column (30) from which dioxolane is withdrawn as a bottom product while the distillate stream of the purification column is recycled to the phase separation unit. An aqueous fraction stream from the phase separation unit is transferred to a waste water column (40), withdrawing a waste water stream from the bottom of the waste water column, withdrawing a side stream (42) from a stage between the feed stage and the reflux stage of the waste water column and recycling this stream (42) to the phase separation unit, and withdrawing a distillate stream (43) containing methanol from the waste water column.

9 Claims, 3 Drawing Sheets

PROCESS FOR PREPARING DIOXOLANE

CROSS-REFERENCE TO RELATED APPLICATIONS

This application is a national stage application (under 35 U.S.C. § 371) of PCT/EP2019/061773, filed May 8, 2019, which claims benefit of European Application No. 18173076.3, filed May 18, 2018, both of which are incorporated herein by reference in their entirety.

The present invention relates to a process for preparing dioxolane by reacting ethylene glycol with an aqueous solution of formaldehyde in the presence of an acid catalyst.

1,3-dioxacyclopentane, hereinafter referred to as "dioxolane", is a derivative of ethylene glycol which is used industrially and can be prepared by reacting ethylene glycol with an aqueous formaldehyde solution in the presence of acid catalysts such as sulfuric acid, boron trifluoride, zinc chloride or acid ion exchangers. Pure dioxolane can be isolated from the reaction mixture using various separation methods, in particular by distillation or extraction.

In the document EP 0 867 434 A1 a process for preparing dioxolane is disclosed in which ethylene glycol and an aqueous formaldehyde solution are reacted in the presence of an acid catalyst. The reaction mixture is fed to a dewatering column where water is removed as the bottom product. At the top of the dewatering column an azeotropic mixture of mainly dioxolane and water is withdrawn and fed to an azeotropic distillation column in which benzene is used to break the azeotrope. The dioxolane product obtained as a bottom product from that column contains benzene which has to be removed in further process steps which are not disclosed in that document. Most of the benzene added is removed from the process and has to be purified for further use or is discharged.

The German patent application DE 10 2005 042 505 A1 discloses a process for preparing dioxolane by reacting ethylene glycol with formaldehyde in aqueous solution in the presence of catalysts, wherein the reaction is carried out in a reactive distillation column. The azeotropic mixture of mainly dioxolane and water is withdrawn from the top of the column and fed to a further distillation column which is operated at an elevated pressure to obtain purified dioxolane as the bottom product. The bottom stream of the reaction column is fed to a further distillation column to separate off the water and to recycle unreacted ethylene glycol. Even though this process does not need any extracting agent like benzene in the previous process, part of the dioxolane produced is lost due to a necessary discharge from the top of the dioxolane purification column.

The processes for preparing dioxolane known in the art require either relatively high amounts of extracting agents that have to be purified in further process steps or are discharged, and/or parts of the valuable product dioxolane is lost.

It was an object of the invention to provide a process for preparing dioxolane which increases the yield of the product dioxolane while reducing the amount of auxiliary substances and waste.

This object is achieved according to the invention by a process for preparing dioxolane according to claim 1. Advantageous embodiments and further developments of the invention are indicated in the dependent claims 2 to 10.

According to the invention, the process for preparing dioxolane comprises the following steps:
a) feeding a first feed stream containing ethylene glycol and a second feed stream containing formaldehyde and methanol in aqueous solution to a reaction distillation device and reacting ethylene glycol and formaldehyde in aqueous solution in the presence of at least one catalyst to obtain a raw product which comprises water, dioxolane and methanol,
b) transferring a distillate stream containing raw product from the top of the reaction distillation device to a phase separation unit, wherein an organic extracting agent is present in the phase separation unit,
c) transferring an organic fraction stream from the phase separation unit to an upper part of a purification column, withdrawing a bottom product stream containing dioxolane from the purification column, and recycling a distillate stream from the purification column to the phase separation unit,
d) transferring an aqueous fraction stream from the phase separation unit to a waste water column, withdrawing a waste water stream from the bottom of the waste water column, withdrawing a side stream from a stage between the feed stage and the reflux stage of the waste water column and recycling this stream to the phase separation unit, and withdrawing a distillate stream containing methanol from the waste water column.

It has been found that the provision of a phase separation unit between the reaction distillation device and the two further columns in combination with the provision of an organic extracting agent simplify the separation of the component mixture, increase the dioxolane purity, facilitate a complete recycle of the extracting agent and minimize losses of valuable product.

Preferably, the inventive process is a continuous process, such that the above-mentioned steps (a) to (d) are performed simultaneously.

The reaction distillation device used in step (a) can be any combination of reaction and distillation that enables the reaction of ethylene glycol and formaldehyde to obtain dioxolane. In one embodiment the reaction distillation device is set up as a reactor that is directly coupled with a distillation column. In a further embodiment the reaction distillation device is set up as a reactive distillation column where the catalyst is embedded on trays or stages of the distillation column, preferably in the lower part of the distillation column. In a further embodiment the reaction distillation device is set up as a reactor directly coupled to a reactive distillation column where catalyst is present in the reactor as well as in a part of the distillation column.

Preferably, the mass fraction of methanol in the distillate stream from the reaction distillation device is from 0.02% to 5% by weight.

It is further preferred that the mass fraction of methanol in the bottom product stream of the purification column is less than 0.5%, more preferably less than 0.1%, most preferably less than 0.05%, in particular less than 0.01%.

Methanol is usually present in small amounts in the feed stream of the aqueous formaldehyde, mainly due to an incomplete conversion of methanol in the formaldehyde production process. Furthermore, methanol acts as a stabilizer for the formalin solution. Despite the small amounts present in the feed stream, it has been found that due to the full recycle of the water methanol accumulates and leads to maloperations in the long run. This problem is not discussed in the prior art at all. The inventive solution of withdrawing a distillate stream containing methanol from the waste water column solves this problem.

In a preferred embodiment an additional side stream containing methanol is withdrawn from a stage below the feed stage of the waste water column. Depending on the operation conditions of the waste water column methanol accumulates in the middle region of the column. The additional side stream withdrawal can be advantageous for the removal of methanol and thus the stable operation of the process.

In a further preferred embodiment an additional water containing stream is fed to the phase separation unit. Water is transferred to the phase separation unit in step (b) of the process according to the invention as it is one component of the distillate stream of the reaction distillation device. The largest part of that water is transferred in the aqueous phase from the phase separation unit to the waste water column. At first glance, it is counter-intuitive to add additional water as it increases the load and hence the operating costs of the waste water column. However, it has been found that adding additional water increases the range of operability of the phase separation unit and therefore has an advantageous effect on a stable operation of the inventive process.

Generally, there is no specific restriction with respect to the composition of the organic extracting agent, provided that it is able to separate dioxolane and water.

In a preferred embodiment the organic extracting agent ("EA") is selected from the group of substances that fulfill the following conditions:

(a) gamma_inf_298_(EA in water)+gamma_inf_298_(water in EA)>1600
(b) gamma_inf_298_(methanol in EA)/gamma_inf_298_(methanol in water)>1.5
(c) gamma_inf_335_(EA in dioxolane)>1
    gamma_inf_335_(EA in water)>1
    gamma_inf_335_(dioxolane in EA)>1
    gamma_inf_335_(water in EA)>1
(d) and additionally
    if $P^0_{DX} > P^0_{EA} > P^0_W$:
    $(P^0_{DX} \cdot \text{gamma\_inf\_335\_(dioxolane in EA)}/P^0_{EA} - 1) \cdot (P^0_{DX}/P^0_{EA}/\text{gamma\_inf\_335\_(EA in dioxolane)} - 1) < 0$
    else if $P^0_W > P^0_{EA}$:
    $(P^0_{DX} \cdot \text{gamma\_inf\_335\_(dioxolane in EA)}/P^0_{EA} - 1) \cdot (P^0_{DX}/P^0_{EA}/\text{gamma\_inf\_335\_(EA in dioxolane)} - 1) < 0$
    and
    $(P^0_W \cdot \text{gamma\_inf\_335\_(water in EA)}/P^0_{EA} - 1) \cdot (P^0_W/P^0_{EA}/\text{gamma\_inf\_335\_(EA in water)} - 1) < 0$ wherein "gamma_inf_<temperature>_(<solute> in <solvent>)" represents the limiting activity coefficient at temperature 298.15 K ("298") or 334.85 K ("335") respectively and the solute at infinite dilution in the solvent, $P^0_k$ denotes the vapor pressure of the pure component k, "DX" denotes dioxolane and 'W' denotes water.

Condition (a) ensures that there exists a miscibility gap in the phase separation unit, which enhances the separation of the organic phase from the aqueous phase. Condition (b) ensures the enrichment of methanol in the aqueous fraction stream leaving the phase separation unit. Conditions (c) guarantee that there are no heavy boiling azeotropes present which would hinder the separation into pure components. Conditions (d) depend on the vapor pressures of the pure components and facilitate an azeotropic distillation. For conditions (d) all pure component vapor pressures are calculated at a temperature of 334.85 K.

Methods and software tools for the determination of pure component vapor pressures and limiting activity coefficients are known in the art. As an example, the pure component vapor pressure data can be derived from a vapor pressure function of experimental data and limiting activity coefficients (activity coefficients at infinite dilution) can be calculated by the quantumchemical continuum solvation model Cosmo-RS (COSMOthermX Version C30_1702, developed and copyright by COSMOlogic GmbH&Co.KG, Imbacher Weg 46, 51379 Leverkusen, Germany) with the parameterization BP_TZVP_C30_1701.

Preferably, the extracting agent is selected from the group consisting of pentane, cyclopentane, 2,2-dimethylbutane, 2,3-dimethylbutane, methylisobutylether, 2-methylpentane, 3-methylpentane, propylisopropylether, hexane, methylcyclopentane, 2,2-dimethylpentane, 2,4-dimethylpentane, cyclohexane, 3,3-dimethylpentane, 2-ethyl-3-methyl-1-butene, 1,1-dimethylcyclopentane, 2-methylhexane, di-n-propylether, (z)-1,3-dimethylcyclopentane, trans-1,2-dimethylcyclopentane, trans-1,3-dimethylcyclopentane, 3-methyl-hexane, 1-ethoxybutane, 3-ethylpentane, 2,2,4-trimethylpentane, n-heptane, isopropyl-isobutyl-ether, (z)-1,2-dimethylcyclopentane, 2,2-dimethylhexane, 2,3-dimethylhexane, 2,4-dimethylhexane, 2,5-dimethylhexane, 3,4-dimethylhexane, 2-methylheptane, octane.

Table 1 shows the values for the pure component vapor pressure and the limiting activity coefficients calculated with the above-mentioned Cosmo-RS model.

TABLE 1

| CAS | Extracting Agent | $P^0_{EA}$ (hPa) | gamma_inf_298 (methanol in water) | gamma_inf_298 (EA in water) | gamma_inf_298 (water in EA) | gamma_inf_298 (methanol in EA) | gamma_inf_335 (EA in diaxolane) | gamma_inf_335 (EA in water) | gamma_inf_335 (dioxolane in EA) | gamma_inf_335 (water in EA) |
|---|---|---|---|---|---|---|---|---|---|---|
| 109-66-0 | pentane | 2976.4 | 2.08 | 37456.79 | 1736.05 | 252.56 | 4.20 | 20026.37 | 4.22 | 216.88 |
| 287-92-3 | cyclopentane | 2010.0 | 2.08 | 9942.67 | 1724.29 | 248.71 | 3.41 | 5727.81 | 4.11 | 216.91 |
| 75-83-2 | 2,2-dimethylbutane | 1942.8 | 2.08 | 55139.59 | 1542.28 | 225.62 | 4.25 | 28378.17 | 3.92 | 195.42 |
| 79-29-8 | 2,3-dimethylbutane | 1532.0 | 2.08 | 62526.32 | 1585.68 | 230.68 | 4.34 | 31946.64 | 3.96 | 199.63 |
| 625-44-5 | methylisobutylether | 1523.3 | 2.08 | 1662.23 | 17.59 | 6.62 | 2.06 | 1841.79 | 1.84 | 14.02 |
| 107-83-5 | 2-methylpentane | 1437.5 | 2.08 | 107555.55 | 1605.80 | 236.09 | 4.74 | 53217.31 | 4.05 | 201.30 |
| 96-14-0 | 3-methylpentane | 1310.3 | 2.08 | 89437.45 | 1624.02 | 237.42 | 4.63 | 44768.54 | 4.05 | 203.23 |
| 627-08-7 | propylisopropylether | 1127.4 | 2.08 | 4318.24 | 10.74 | 4.76 | 2.45 | 5250.47 | 1.94 | 10.80 |
| 110-54-3 | hexane | 1110.7 | 2.08 | 142926.87 | 1614.18 | 238.99 | 4.98 | 69637.22 | 4.10 | 202.14 |
| 96-37-7 | methylcyclopentane | 1012.9 | 2.08 | 34293.42 | 1594.99 | 236.04 | 4.04 | 18078.07 | 4.03 | 201.07 |
| 590-35-2 | 2,2-dimethylpentane | 806.0 | 2.08 | 217277.94 | 1457.58 | 216.23 | 5.01 | 101591.07 | 3.82 | 184.64 |
| 108-08-7 | 2,4-dimethylpentane | 771.3 | 2.08 | 255208.76 | 1475.48 | 218.78 | 5.13 | 118163.02 | 3.85 | 186.28 |
| 110-82-7 | cyclohexane | 765.5 | 2.08 | 21250.58 | 1677.45 | 248.06 | 3.88 | 11531.27 | 4.17 | 209.50 |
| 562-49-2 | 3,3-dimethylpentane | 652.9 | 2.08 | 159080.62 | 1494.68 | 220.24 | 4.84 | 75848.01 | 3.86 | 188.49 |
| 7357-93-9 | 2-ethyl-3-methyl-1-butene | 637.5 | 2.08 | 86467.19 | 872.84 | 126.49 | 3.22 | 43581.11 | 2.67 | 127.96 |
| 1638-26-2 | 1,1-dimethylcyclopentane | 615.8 | 2.08 | 75017.65 | 1451.99 | 215.83 | 4.31 | 37191.63 | 3.80 | 184.66 |
| 591-76-4 | 2-methylhexane | 567.4 | 2.08 | 397375.92 | 1501.63 | 223.94 | 5.53 | 179452.11 | 3.92 | 188.76 |
| 111-43-3 | di-n-propylether | 562.8 | 2.08 | 9221.18 | 19.86 | 7.75 | 2.83 | 10223.21 | 2.21 | 17.50 |
| 2532-58-3 | (z)-1,3-dimethylcyclopentane | 552.4 | 2.08 | 118902.09 | 1509.16 | 227.15 | 4.76 | 57302.57 | 3.96 | 190.06 |
| 1759-58-6 | trans-1,3-dimethylcyclopentane | 548.8 | 2.08 | 117626.60 | 1524.72 | 228.83 | 4.76 | 56783.50 | 3.98 | 191.62 |
| 822-50-4 | trans-1,2-dimethylcyclopentane | 542.3 | 2.08 | 96521.08 | 1501.35 | 223.65 | 4.54 | 47166.27 | 3.89 | 189.40 |
| 589-34-4 | 3-methyl-hexane | 534.9 | 2.08 | 316456.93 | 1522.61 | 225.58 | 5.35 | 141931.16 | 3.93 | 190.88 |
| 628-81-9 | 1-ethoxybutane | 523.7 | 2.08 | 5925.37 | 12.94 | 5.52 | 2.56 | 6953.94 | 2.00 | 12.32 |
| 617-78-7 | 3-ethylpentane | 510.2 | 2.08 | 213827.47 | 1544.47 | 228.33 | 5.12 | 100108.48 | 3.96 | 193.07 |
| 540-84-1 | 2,2,4-trimethylpentane | 432.7 | 2.08 | 473882.91 | 1372.04 | 205.20 | 5.39 | 208111.28 | 3.68 | 174.26 |
| 142-82-5 | n-heptane | 430.0 | 2.08 | 553431.20 | 1514.42 | 227.26 | 5.85 | 245210.87 | 3.97 | 189.96 |
| 78448-33-6 | isopropyl-isobutyl-ether | 425.6 | 2.08 | 26507.09 | 16.49 | 6.82 | 3.11 | 24397.28 | 2.24 | 16.56 |
| 1192-18-3 | (z)-1,2-dimethylcyclohexane | 424.6 | 2.08 | 80876.95 | 1511.09 | 225.76 | 4.48 | 39910.09 | 3.93 | 190.38 |
| 590-73-8 | 2,2-dimethylhexane | 332.0 | 2.08 | 829096.62 | 1389.56 | 208.76 | 5.87 | 352608.12 | 3.73 | 175.89 |
| 592-13-2 | 2,5-dimethylhexane | 305.8 | 2.08 | 1120095.03 | 1422.77 | 214.14 | 6.21 | 466796.72 | 3.80 | 178.95 |
| 589-43-5 | 2,4-dimethylhexane | 303.7 | 2.08 | 836816.00 | 1417.23 | 211.67 | 5.89 | 355691.60 | 3.75 | 178.53 |
| 584-94-1 | 2,3-dimethylhexane | 247.2 | 2.08 | 823284.54 | 1433.33 | 214.48 | 5.93 | 347782.02 | 3.80 | 180.22 |
| 583-48-2 | 3,4-dimethylhexane | 231.1 | 2.08 | 695543.14 | 1444.38 | 215.95 | 5.83 | 299269.98 | 3.81 | 181.37 |
| 592-27-8 | 2-methylheptane | 227.0 | 2.08 | 1445518.27 | 1427.29 | 215.50 | 6.44 | 585092.95 | 3.82 | 179.45 |
| 111-65-9 | octane | 169.9 | 2.08 | 2109091.58 | 1429.29 | 216.72 | 6.81 | 848617.99 | 3.85 | 179.61 |

More preferably, the extracting agent is selected from the group consisting of isomers of hexane ($C_6H_{14}$). Isomers of hexane are n-hexane, 2-methylpentane, 3-methylpentane, 2,3-dimethylbutane and 2,2-dimethylbutane. The extracting agent may comprise a single isomer or a mixture of isomers of hexane. Further substances can be present in the extracting agent, for example other $C_6$ hydrocarbons like cyclohexane or methylcyclopentane ($C_6H_{12}$).

Even more preferably, the extracting agent comprises n-hexane with a mass fraction of at least 80%, preferably at least 90%, more preferably at least 95%, in particular at least 99%. Particularly preferred technically pure grades of hexane typically contain 99% or more of n-hexane and amounts of up to 1% in total of various $C_6$ isomers, including cyclohexane and methylcyclopentane. A high purity of n-hexane is preferred to avoid an accumulation of side component in the extracting agent.

In a further preferred embodiment a make-up stream containing the organic extracting agent is fed to the phase separation unit. One advantage of the process according to the invention over the prior art is the full recycle of the extracting agent by design and consequently no loss of extracting agent. The extracting agent has to be provided at the startup of the process once. Afterwards, the extracting agent stays in the process. However, due to operational disturbances or malfunctions, it might happen that extracting agent is withdrawn from the process in an outgoing stream. Thus, the provision of a make-up stream of extracting agent is advantageous for a stable operation of the process. Generally, the make-up stream can be fed to any process stream or process unit. Preferably, the make-up stream is fed to the phase separation unit. More preferably, the make-up stream is fed to a mixing device of the phase separation unit.

In a preferred embodiment of the process according to the invention the phase separation unit comprises a mixer and a phase separator. The distillate stream from the reaction distillation device, the distillate stream from the purification column, the side stream from the waste water column and optionally the additional water containing stream and/or the make-up stream containing the organic extracting agent are fed to and mixed in the mixer. The outlet stream of the mixer is fed to the phase separator. Mixing the streams in a first step and separating the phases in a second step has the advantage that the mixture fed to the phase separator is more homogeneous, e.g. in terms of droplet size, compared to feeding the streams directly into the phase separator without mixing step. The mixer can be any kind of mixing device that provides a thorough and homogeneous mixture. Preferably, the mixer is a static mixer. In a further preferred embodiment the mixed stream in the outlet of the mixer is fed to a cooling device where the temperature of the mixed stream is reduced before it is fed to the phase separator. Reducing the temperature of the mixed stream facilitates a stable operation of the phase separation.

The process according to the invention provides several advantages of the process known in the prior art. Dioxolane is produced and provided in a very high purity without significant loss of product via other streams. Side components, especially methanol, is efficiently removed. The extracting agent used is recycled without material loss. The process can be operated in a stable and reliable manner on an industrial and commercial scale.

The invention will be illustrated below with the aid of the drawings; the drawings are to be interpreted as an in-principle presentation. They do not constitute any restriction of the invention, for example in respect of specific dimensions or design variants of components. In the figures.

LIST OF REFERENCE NUMERALS USED

Figure 1:
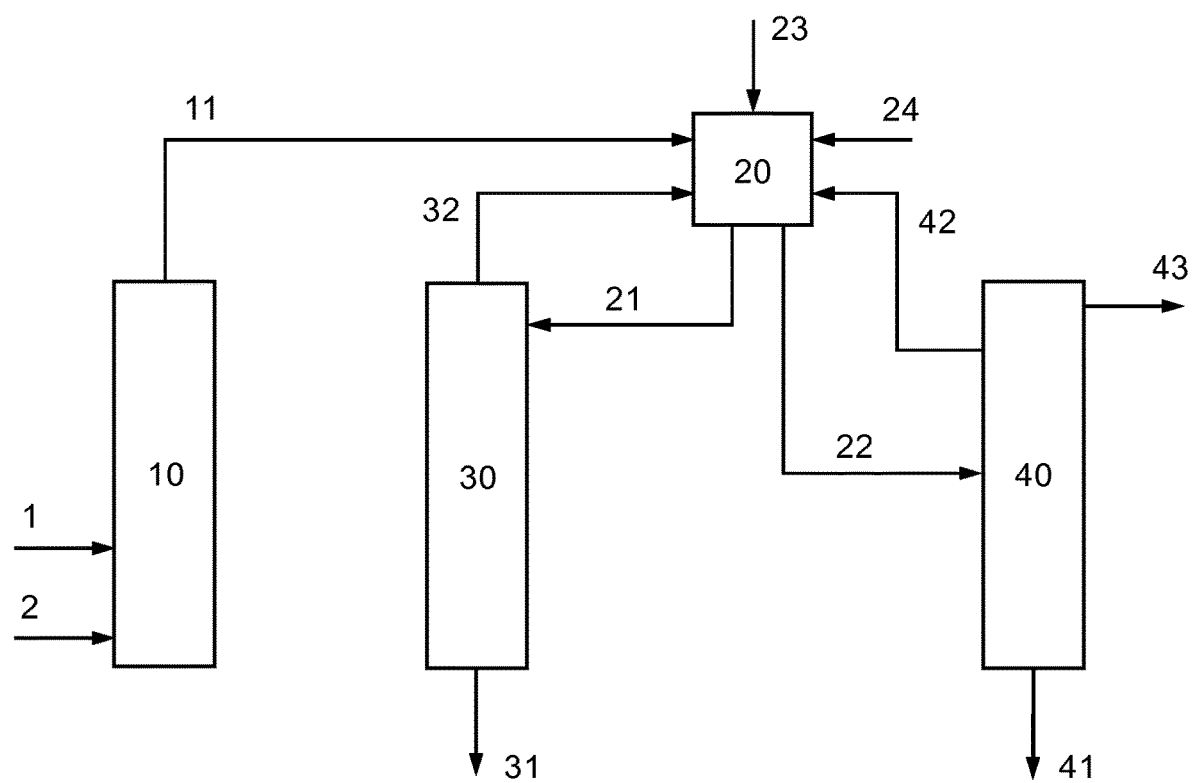
FIG. 1 shows a block diagram of a first embodiment of the process according to the invention.

1 . . . feed stream containing ethylene glycol
2 . . . feed stream containing formaldehyde and methanol in aqueous solution
10 . . . reaction distillation device
11 . . . distillate stream of reaction distillation device
20 . . . phase separation unit
21 . . . organic fraction stream
22 . . . aqueous fraction stream
23 . . . water containing stream
24 . . . make-up stream of organic extraction agent
25 . . . mixer
26 . . . phase separator
27 . . . cooling device
30 . . . purification column
31 . . . bottom product stream of the purification column
32 . . . distillate stream of the purification column
40 . . . waste water column
41 . . . waste water stream
42 . . . side stream from the waste water column
43 . . . distillate stream from the waste water column
44 . . . side stream containing methanol from the waste water column FIG. 1 shows a block diagram of a first embodiment of the process according to the invention. The block diagram only shows the main operation units. Auxiliary equipment like reboilers, condensers, pumps, valves and instrumentation equipment is not depicted in FIG. 1.

In a continuous process for the preparation of dioxolane, a feed stream 1 containing ethylene 40 glycol and a feed stream 2 containing formaldehyde and methanol in an aqueous solution are fed into the lower region of a reaction distillation device 10. At least one catalyst is present in the reaction distillation device 10, preferably in the lower part of the device. The catalyst enables the reaction of ethylene glycol and formaldehyde in aqueous solution to form a raw reaction product which comprises water, dioxolane and methanol. The raw product is withdrawn from the top of the reaction distillation device 10, part of it is condensed and recycled as reflux to the reaction distillation device 10 (not shown), and the remainder is transferred as distillate stream 11 to a phase separation unit 20.

In the phase separation unit 20 an organic extracting agent is present that enhances the separation of the inflowing substances into an aqueous fraction and an organic fraction. The organic fraction is withdrawn from the phase separation unit 20 in stream 21 and is transferred to an upper part of a purification column 30. The aqueous fraction is withdrawn from the phase separation unit 20 in stream 22 and is transferred to a waste water column 40.

The purification column 30 is equipped with a reboiler (not shown) that evaporates parts of the material present in the bottom part of the column such that there is a counter flow regime of the organic material fed in stream 21 and the vapor produced in the reboiler inside the column. The remaining part of the material in the bottom of the purification column 30 is withdrawn as bottom product stream 31 which is rich in dioxolane. The up-flowing material is withdrawn as a distillate stream 32 from the purification column 30 and is recycled to the phase separation unit 20.

The aqueous fraction stream 22 from the phase separation unit 20 is fed to a middle section of the waste water column 40. The column is equipped with a reboiler and a condenser (not shown) that enable a counter flow regime of liquid and vapor in the column. Part of the liquid material in the bottom of the column is withdrawn as a water rich waste water stream 41. The remainder is fed to the reboiler. The overhead stream leaving the top of the waste water column 40 is fed to the condenser. The main part of the condensed material is recycled as reflux to the column. The remainder is withdrawn as a distillate stream 43 containing methanol. A side stream 42 is withdrawn from a stage between the feed stage and the reflux stage of the waste water column 40 and is recycled to the phase separation unit 20. Optionally, an additional water containing stream 23 and/or a make-up stream 24 containing the organic extracting agent is fed to the phase separation unit 20.

Figure 2:
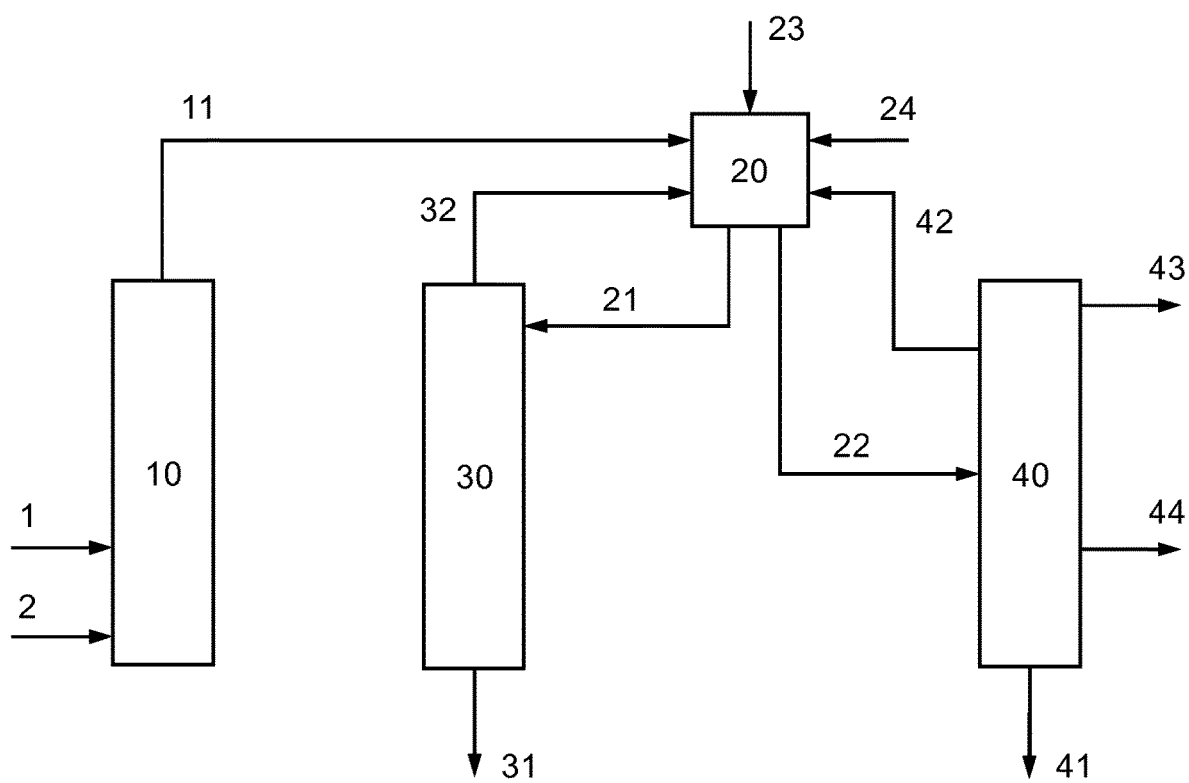
FIG. 2 shows a block diagram of a second embodiment of the process according to the invention.

FIG. 2 shows a block diagram of a second embodiment of the process according to the invention. This process is a modification of the first embodiment shown in FIG. 1. The main difference is an additional side stream 44 containing methanol which is withdrawn from a stage below the feed stage of the waste water column 40. One advantage of this embodiment is that the additional side stream 44 contains methanol but merely no dioxolane. Thus, the methanol load of the upper part of the waste water column 40 is reduced which allows to reduce the distillate stream 43 compared to the first embodiment shown in FIG. 1.

Figure 3:
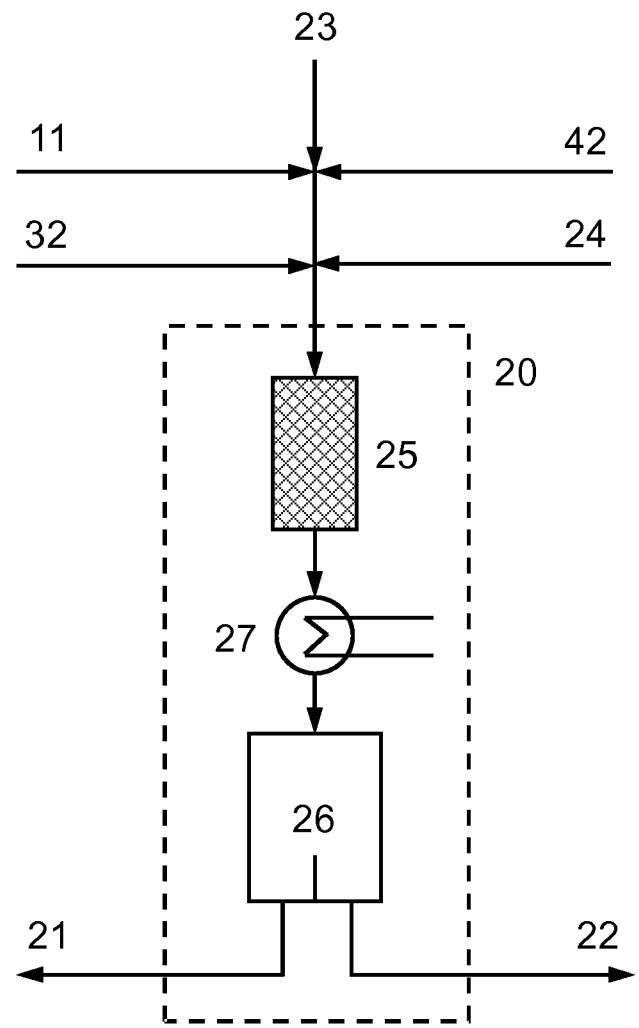
FIG. 3 shows a preferred embodiment of a phase separation unit according to the invention.

FIG. 3 shows a preferred embodiment of a phase separation unit 20 according to the invention. The phase separation unit 20 comprises a mixer 25 and a phase separator 26. The distillate stream 11 from the reaction distillation device, the distillate stream 32 from the purification column and the side stream 42 from the waste water column are fed to the mixer 25. Optionally, the additional water containing stream 23 and/or the make-up stream 24 containing the organic extracting agent are fed to the mixer 25 as well. All streams are mixed in the mixer 25, the outlet stream of the mixer is fed to a cooling device 27 where the temperature of the mixed stream is reduced, and the outlet stream of the cooling device 27 is fed to the phase separator 26.

EXAMPLE

An experiment on an industrial scale was operated for more than nine days in a continuous setup according to FIG. 1 under stable production conditions.

The reaction distillation device 10 was set up as a reactor directly coupled to a distillation column with 30 trays. 145 kg/h of an aqueous solution containing 65 wt % of formaldehyde and 0.6 wt % of methanol were continuously fed to the reactor. 185 kg/h ethylene glycol were continuously fed to the 10th tray (counting from the top) of the distillation column and was in counter-current flow to the dioxolane raw product flowing out of the reactor. Sulfuric acid was used as catalyst, its concentration being 2 wt % with respect to the reactor content.

A distillate stream 11 containing the raw product was transferred from the top of the reaction distillation device 10 to a phase separation unit 20. The phase separation unit comprised a static mixer 25 and a phase separator 26. An additional water stream 23 was fed to the mixer at a feed rate of 205 kg/h. n-Hexane had been filled into the plant during start-up as an organic extracting agent. The mass fraction of n-hexane in the organic extracting agent was 99% with isomers of n-hexane ($C_6H_{14}$) and $C_6H_{12}$ components summing up to the remaining 1%. During the test run of nine days it was not necessary to provide a make-up stream 24 containing extracting agent.

With respect to the criteria for the selection of a suitable extracting agent, the n-hexane used fulfills the following criteria:

(a) gamma_inf_298_(EA in water)+gamma_inf_298_(water in EA)=72271>1600
(b) gamma_inf_298_(methanol in EA)/gamma_inf_298_(methanol in water)=114.9>1.5
(c) gamma_inf_335_(EA in dioxolane)=4.98>1
  gamma_inf_335_(EA in water)=69637>1
  gamma_inf_335-(dioxolane in EA)=4.1>1
  gamma_inf_335-(water in EA)=202.14>1

As the pure component vapor pressure (calculated at a temperature of 334.85 K) for n-hexane is larger than that for dioxolane ($P^0_{EA}$=1110.7 hPa, $P^0_{DX}$=905.6 hPa), no further criteria have to be satisfied.

An organic fraction stream 21 was transferred from the phase separation unit 20 to the uppermost tray of the purification column 30. The distillate stream 32 was recycled to the mixer 25 of the phase separation unit 20. From the bottom of the column dioxolane with a purity of 99.9 wt % was withdrawn as a bottom product stream 31 at a rate of 190 kg/h. The water content in the dioxolane product was 43 ppm. The methanol content was 69 ppm. No extracting agent (n-hexane) was detected in the dioxolane product.

A stream 22 containing the aqueous fraction of the phase separator was transferred to the 20th tray (counting from top with 30 trays in total) of the waste water column 40. A waste water stream 41 was withdrawn from the bottom of that column with a water content of 98.3 wt %. Non-reacted formaldehyde (1.6 wt %) was also discharged with the waste water stream 41. A side stream 42 was withdrawn from tray 10 of the waste water column and recycled to the mixer 25. The distillate stream 43 from the waste water column was condensed and partially recycled to the top of the column as a reflux stream. The remaining portion of the distillate stream 43 was withdrawn from the waste water column at a rate of 28.5 kg/h. This stream contained 85.5 wt % dioxolane, 9.1 wt % water, 0.9 wt % methanol as well as minor amounts of formaldehyde and n-hexane.

In the experiment on an industrial scale, dioxolane was produced with an excellent purity under stable production conditions. No extracting agent (n-hexane) was detected in the dioxolane product. The waste water quality was well in spec at all times during the nine days run-time of the experiment. Some fluctuations in the side-cut flow from the waste water column were observed which led to further fluctuations in the composition of the organic phase and the aqueous phase in the phase separator of up to 10 wt %. However, these fluctuations had no impact on the overall process in general and on the quality of the dioxolane product in particular. Thus, the inventive process turned out to be very robust with regard to disturbances.

Comparative Example

The example according to the invention is compared with Example 4 of the document EP 0 867 434 A1. The main differences are the column configuration in terms of column sequence and the lack of a phase separation unit in the prior art, as well as in the selection of the extracting agent.

In the comparative example, 85 g/h of formalin (60 wt % formaldehyde in aqueous solution) are fed to a reactor which is coupled to a distillation column. 106 g/h of ethylene glycol is fed to the distillation column and flows countercurrently to the dioxolane raw product flowing out of the reactor. A distillate stream at a rate of 191 g/h with mass fractions of 65.4 wt % of dioxolane, 33.7 wt % of water and 0.1 wt % of formaldehyde is withdrawn from the first distillation column and is fed to a dewatering column. In that dewatering column, water is withdrawn from the bottom and a distillate stream at a rate of 136 g/h of an azeotropic mixture containing 91.8 wt % dioxolane and 7.6 wt % water is withdrawn and fed to a purification column. In order to break the azeotrope, benzene is added as an extracting agent at a flow rate of 16 g/h to the purification column. Dioxolane is obtained as a bottom product from the purification column at a flow rate of 135 g/h with a benzene concentration of 11 wt % in the dioxolane product stream. The water content was 44 ppm.

Compared to this prior art example, the process according to the invention provides a significantly higher purity of the desired dioxolane product. As a further advantage of the inventive process, the extracting agent is nearly completely used in internal recycles. An expensive treatment or processing of the extracting agent is not necessary in the inventive process—in contrast to the process of the prior art.

The invention claimed is:

1. A process for preparing dioxolane comprising the steps of
    a) feeding a first feed stream (1) containing ethylene glycol and a second feed stream (2) containing formaldehyde and methanol in aqueous solution to a reaction distillation device (10) and reacting ethylene glycol and formaldehyde in aqueous solution in the presence of at least one catalyst to obtain a raw product which comprises water, dioxolane and methanol,
    b) transferring a distillate stream (11) containing raw product from the top of the reaction distillation device (10) to a phase separation unit (20), wherein an organic extracting agent is present in the phase separation unit (20), wherein the mass fraction of methanol in the distillate stream (11) from the reaction distillation device (10) is from 0.02% to 5%,
    c) transferring an organic fraction stream (21) from the phase separation unit (20) to an upper part of a purification column (30), withdrawing a bottom product stream (31) containing dioxolane from the purification column (30), and recycling a distillate stream (32) from the purification column (30) to the phase separation unit (20), wherein the mass fraction of methanol in the bottom product stream (31) of the purification column (30) is less than 0.5%,
    d) transferring an aqueous fraction stream (22) from the phase separation unit (20) to a waste water column (40), withdrawing a waste water stream (41) from the bottom of the waste water column (40), withdrawing a side stream (42) from a stage between the feed stage and the reflux stage of the waste water column (40) and recycling this stream (42) to the phase separation unit (20), and withdrawing a distillate stream (43) containing methanol from the waste water column (40).

2. The process according to claim 1, wherein a side stream (44) containing methanol is withdrawn from a stage below the feed stage of the waste water column (40).

3. The process according to claim 1, wherein an additional water containing stream (23) is fed to the phase separation unit (20).

4. The process according to claim 1, wherein the extracting agent is selected from the group consisting of pentane, cyclopentane, 2,2-dimethylbutane, 2,3-dimethylbutane, methylisobutylether, 2-methylpentane, 3-methylpentane, propylisopropylether, hexane, methylcyclopentane, 2,2-dimethylpentane, 2,4-dimethylpentane, cyclohexane, 3,3-dimethylpentane, 2-ethyl-3-methyl-1-butene, 1,1-dimethylcyclopentane, 2-methylhexane, di-n-propylether, (z)-1,3-dimethylcyclopentane, trans-1,2-dimethylcyclopentane, trans-1,3-dimethylcyclopentane, 3-methyl-hexane, 1-ethoxybutane, 3-ethylpentane, 2,2,4-trimethylpentane, n-heptane, isopropyl-isobutyl-ether, (z)-1,2-dimethylcyclopentane, 2,2-dimethylhexane, 2,3-dimethylhexane, 2,4-dimethylhexane, 2,5-dimethylhexane, 3,4-dimethylhexane, 2-methylheptane, and octane.

5. The process according to claim 1, wherein the extracting agent is selected from the group consisting of isomers of hexane ($C_6H_{14}$).

6. The process according to claim 1, wherein the extracting agent comprises n-hexane with a mass fraction of at least 80%.

7. The process according to claim 1, wherein a make-up stream (24) containing the organic extracting agent is fed to the phase separation unit (20).

8. The process according to claim 1, wherein the phase separation unit (20) comprises a mixer (25) and a phase separator (26), the distillate stream (11) from the reaction distillation device (10), the distillate stream (32) from the purification column (30), the side stream (42) from the waste water column (40) and optionally the additional water containing stream (23) and/or the make-up stream (24) containing the organic extracting agent being fed to and mixed in the mixer (25), and the outlet stream of the mixer (25) being fed to the phase separator (26).

9. The process according to claim 1, wherein the mass fraction of methanol in the bottom product stream (31) of the purification column (30) is less than 0.1%.

* * * * *